US012724016B2

(12) United States Patent
Da et al.

(10) Patent No.: US 12,724,016 B2
(45) Date of Patent: Sep. 1, 2026

(54) METHOD FOR CALCULATING CARBON EMISSION OF BOILER

(71) Applicant: China Special Equipment Inspection & Research Institute, Beijing (CN)

(72) Inventors: Yaodong Da, Beijing (CN); Xuemin Liu, Beijing (CN); Zhenchuan Wang, Beijing (CN); Yongqiang Chang, Beijing (CN)

(73) Assignee: China Special Equipment Inspection & Research Institute, Beijing (CN)

( * ) Notice: Subject to any disclaimer, the term of this patent is extended or adjusted under 35 U.S.C. 154(b) by 314 days.

(21) Appl. No.: 18/404,541

(22) Filed: Jan. 4, 2024

(65) Prior Publication Data

US 2025/0027922 A1 Jan. 23, 2025

(30) Foreign Application Priority Data

Jul. 21, 2023 (CN) ......................... 202310897535.2

(51) Int. Cl.
*G01N 33/00* (2006.01)

(52) U.S. Cl.
CPC ................................ *G01N 33/0027* (2013.01)

(58) Field of Classification Search
CPC .. G01N 33/0027; G01N 33/004; G06F 17/10; G06Q 50/26
See application file for complete search history.

(56) References Cited

U.S. PATENT DOCUMENTS

2024/0183526 A1* 6/2024 Almajed ............. G01M 99/005

FOREIGN PATENT DOCUMENTS

CN 114596072 A * 6/2022 ............. G06Q 50/26
PL 233008 B1 * 8/2019

OTHER PUBLICATIONS

Translation of CN114596072A (Year: 2022).*
Translation of PL233008B1 (Year: 2019).*

* cited by examiner

*Primary Examiner* — Thomas M Hammond, III
(74) *Attorney, Agent, or Firm* — OPENPTO US LLC; Yuhao Liang

(57) ABSTRACT

A method for calculating carbon emission of a boiler is provided. First, a test boundary and emission sources are determined, and the emission sources in the test boundary are divided into direct carbon emission sources and indirect carbon emission sources. Then, combined with a boiler thermal performance test, the carbon emission of each emission source is tested and calculated, so as to obtain a total carbon emission of the boiler per hour in a test period. Finally, a carbon emission intensity of the boiler per unit output heat is calculated according to the total carbon emission of the boiler per hour in the test period. Different test boundaries and emission sources are fully considered, so that quantification requirements of carbon emission of different boiler systems can be met, and meanwhile, the accurate quantification of carbon emission of a boiler is realized.

3 Claims, 3 Drawing Sheets

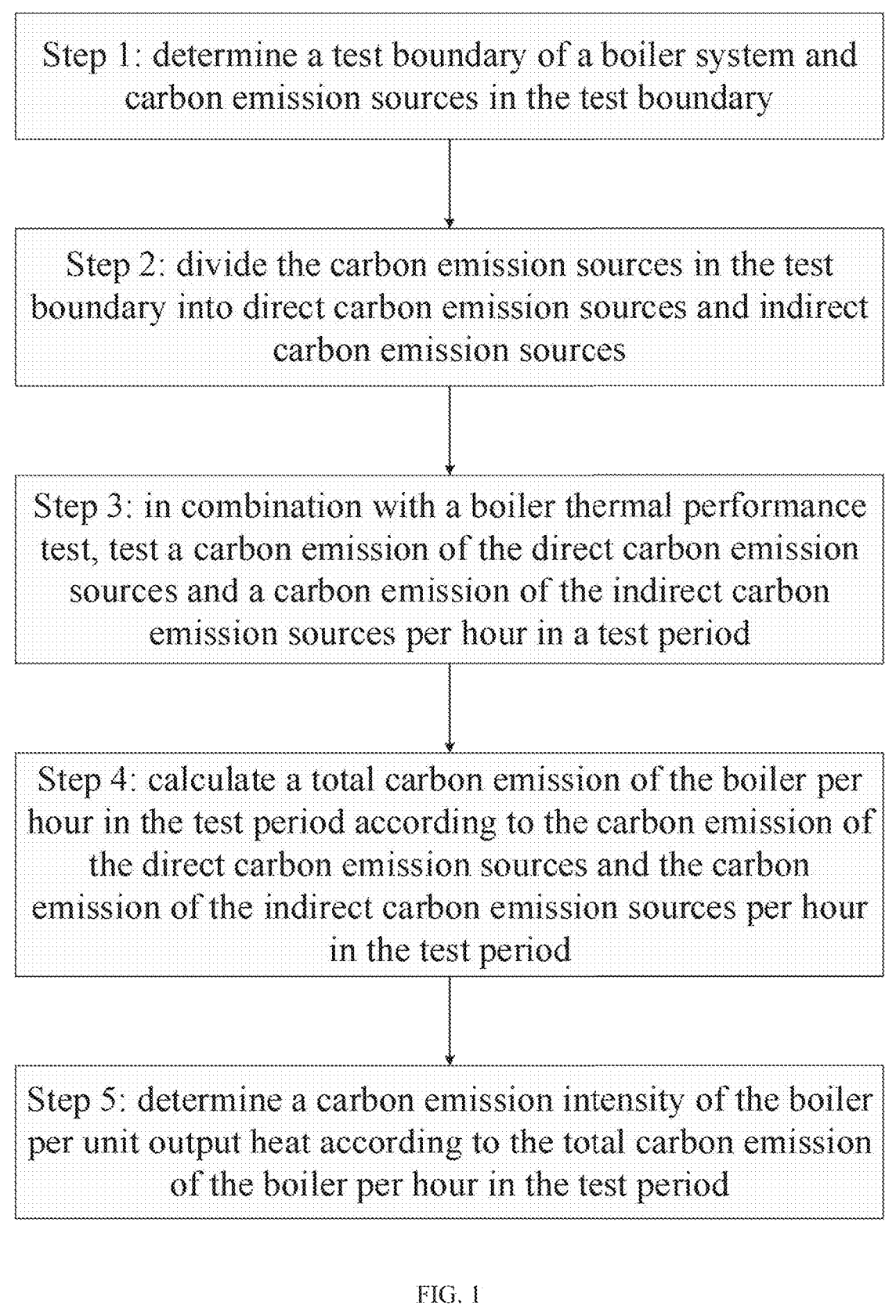

Step 1: determine a test boundary of a boiler system and carbon emission sources in the test boundary Step 2: divide the carbon emission sources in the test boundary into direct carbon emission sources and indirect carbon emission sources Step 3: in combination with a boiler thermal performance test, test a carbon emission of the direct carbon emission sources and a carbon emission of the indirect carbon emission sources per hour in a test period Step 4: calculate a total carbon emission of the boiler per hour in the test period according to the carbon emission of the direct carbon emission sources and the carbon emission of the indirect carbon emission sources per hour in the test period Step 5: determine a carbon emission intensity of the boiler per unit output heat according to the total carbon emission of the boiler per hour in the test period

FIG. 1

METHOD FOR CALCULATING CARBON EMISSION OF BOILER

CROSS-REFERENCE TO RELATED APPLICATION

This patent application claims the benefit and priority of Chinese Patent Application No. 202310897535.2 filed with the China National Intellectual Property Administration on Jul. 21, 2023, the disclosure of which is incorporated by reference herein in its entirety as part of the present application.

TECHNICAL FIELD

The present disclosure relates to the technical field of carbon emission, in particular to a method for calculating carbon emission of a boiler.

BACKGROUND

Boiler consumes a large amount of energy such as coal, oil, natural gas and electricity in use, resulting in a large amount of greenhouse gas emission. On the basis of the existing boiler thermal performance test, the carbon emission test of the boiler can determine a boiler energy efficiency level, and at the same time, obtain a total amount of greenhouse gas emission and the greenhouse gas emission intensity per unit output heat under the rated working conditions and other working conditions of the boiler, which is helpful to establish an evaluation system that organically combines energy efficiency and carbon emission, strengthen the elimination and treatment of the boilers with a high carbon emission intensity, promote the green manufacturing of the boilers, and realize energy saving and carbon reduction.

However, at present, there is only an accounting method for the total amount of greenhouse gas emission at an enterprise level, and there is no accurate quantitative method for carbon emission of the boiler products and devices, which is not conducive to describing and comparing the carbon emission performance of different products. Therefore, it is urgent to establish a method for testing and calculating carbon emission of boiler, which should be coordinated with the existing boiler thermal performance test method, so as to provide a feasible and reasonable method for quantifying carbon emission of boiler for the industry, lay a foundation for building an evaluation system that organically combines energy efficiency and carbon emission, and promote energy saving and carbon reduction of boiler in use.

SUMMARY

The present disclosure aims to provide a method for calculating carbon emission of a boiler, which can realize accurate quantification of carbon emission of a boiler.

In order to achieve the above purpose, the present disclosure provides the following solution.

A method for calculating carbon emission of a boiler includes:

- determining a test boundary of a boiler system and carbon emission sources in the test boundary;
- dividing the carbon emission sources in the test boundary into direct carbon emission sources and indirect carbon emission sources;

- combined with a boiler thermal performance test, testing a carbon emission of the direct carbon emission sources and a carbon emission of the indirect carbon emission sources per hour in a test period;
- calculating a total carbon emission of the boiler per hour in the test period according to the carbon emission of the direct carbon emission sources and the carbon emission of the indirect carbon emission sources per hour in the test period; and
- determining a carbon emission intensity of the boiler per unit output heat according to the total carbon emission of the boiler per hour in the test period.

According to the specific embodiments of the present disclosure, the present disclosure discloses the following technical effects.

The present disclosure disclose a method for calculating carbon emission of a boiler. First, a test boundary and emission sources are determined, and the emission sources in the test boundary are divided into direct carbon emission sources and indirect carbon emission sources. Then, combined with a boiler thermal performance test, the carbon emission of each emission source is tested and calculated, so as to obtain a total carbon emission of the boiler per hour in a test period. Finally, a carbon emission intensity of the boiler per unit output heat is calculated according to the total carbon emission of the boiler per hour in the test period. According to the present disclosure, different test boundaries and emission sources are fully considered, so that quantification requirements of carbon emission of different boiler systems can be met, and at the same time, the accurate quantification of boiler carbon emission is realized.

BRIEF DESCRIPTION OF THE DRAWINGS

In order to explain the embodiments of the present disclosure or the technical solution in the prior art more clearly, the drawings needed in the embodiments will be briefly introduced hereinafter. It is apparent that the drawings described below are only some embodiments of the present disclosure. Other drawings can be obtained according to these drawings without inventive work for those skilled in the art.

FIG. 1 is a flow chart of a method for calculating carbon emission of a boiler according to an embodiment of the present disclosure.

DETAILED DESCRIPTION OF THE EMBODIMENTS

The technical solution in the embodiments of the present disclosure will be clearly and completely described hereinafter with reference to the accompanying drawings in the embodiments of the present disclosure. It is apparent that the described embodiments are only a portion of the embodiments of the present disclosure, rather than all of the embodiments. Based on the embodiments in the present disclosure, all other embodiments obtained by those skilled in the art without inventive work belong to the protection scope of the present disclosure.

The purpose of the present disclosure is to provide a method for calculating carbon emission of a boiler, which combines the existing boiler thermal performance test method to test and calculate the total amount of carbon dioxide emission and the carbon emission intensity per unit output heat under the rated working condition or other working conditions of the boiler, and has practical significance and practical value for boiler manufacturers, users and testing institutions to accurately quantify the carbon emission of the boiler.

In order to make the above purposes, features and advantages of the present disclosure more apparent and understandable, the present disclosure will be further described in detail with the accompanying drawings and specific embodiments.

Figure 2:
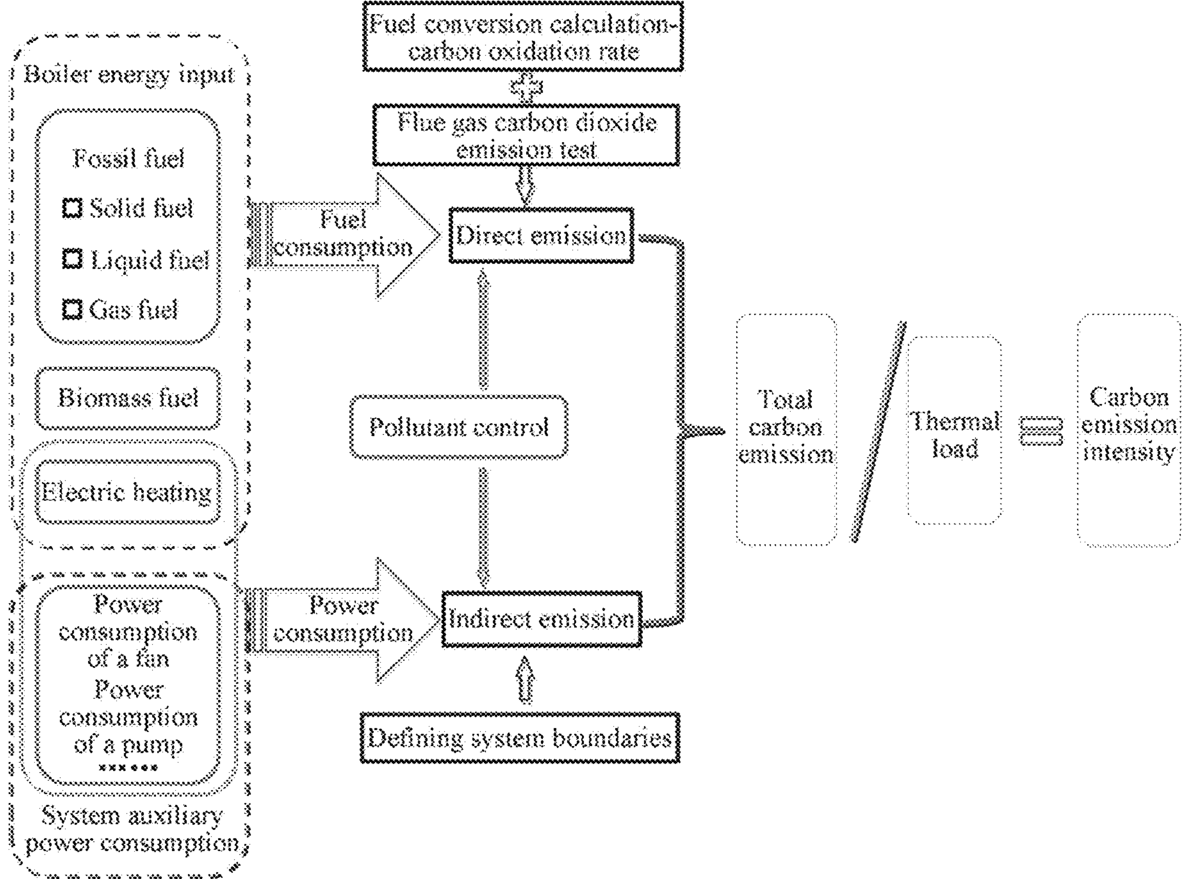
FIG. 2 is a schematic diagram of a method for calculating carbon emission of a boiler according to an embodiment of the present disclosure.

As shown in FIGS. 1 and 2, a method for calculating carbon emission of a boiler according to an embodiment of the present disclosure includes the following steps.

Step 1: a test boundary of a boiler system and carbon emission sources in the test boundary are determined.

Figure 3:
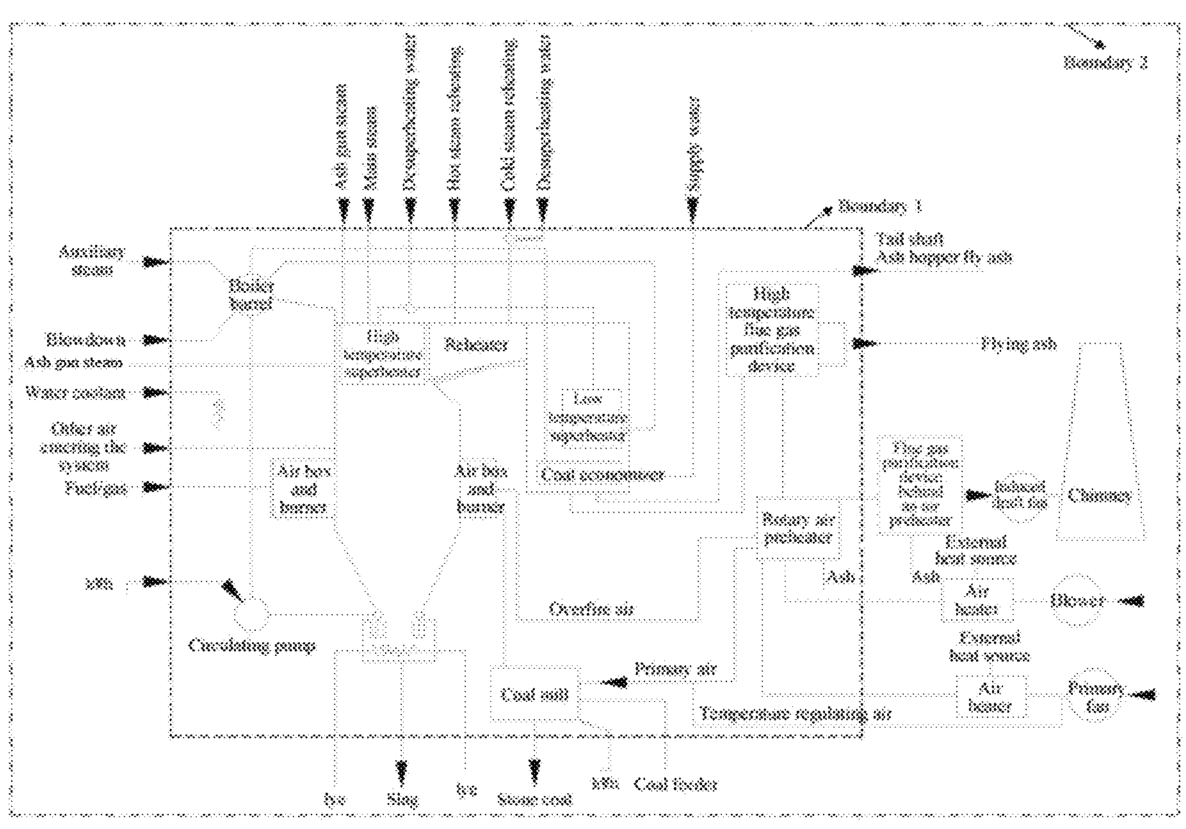
FIG. 3 is a typical boiler system boundary diagram according to an embodiment of the present disclosure.

Referring to FIG. 3, the test boundary includes two types of boundaries.

Boundary 1: a boiler heat balance system boundary. The boiler heat balance system includes a boiler proper, a steam water system circulating pump, a direct-fired pulverizing system coal mill, a denitration device, a flue gas recirculation fan and a slag cooler (when heat is effectively utilized), etc.

Boundary 2: a boiler system boundary. The boiler system includes the boiler proper and various auxiliary devices such as a fan, a pump, a fuel preparation device, a fuel supply device, an ash and slag removal device, a flue gas purification device and a control device, in which the working medium side boundary uses a heat balance boundary.

The emission sources include the boiler proper and various auxiliary devices in the boiler system.

When the test boundary is the Boundary 1, the direct carbon emission generated by fuel (excluding biomass) combustion and desulfurization and denitrification in the boiler heat balance system boundary can be only calculated, and it is also possible to calculate the direct carbon emission generated by fuel (excluding biomass) combustion and desulfurization and denitrification in the boiler heat balance system boundary, as well as the indirect carbon emission generated by power consumption of an electric heating device and an auxiliary device in the boiler heat balance system and the corresponding indirect carbon emission generated by power consumption of an auxiliary device outside the system to overcome the flow resistance of flue gas and steam water in the boiler heat balance system. When the test boundary is the Boundary 2, it can be possible to calculate the direct carbon emission generated by fuel (excluding biomass) combustion and desulfurization and denitrification and the indirect carbon emission generated by power consumption of all related electric heating devices and auxiliary devices within the boiler system boundary.

For fossil fuel-fired boilers, their direct carbon emission are much greater than the indirect carbon emission. When a quantification purpose is mainly to compare the characteristics of different fuel emissions and it is difficult to determine the auxiliary power consumption, the direct carbon emission generated by fuel (excluding biomass) combustion and desulfurization and denitrification within the boiler heat balance system boundary can be only calculated.

Step 2: the carbon emission sources within the test boundary are divided into direct carbon emission sources and indirect carbon emission sources.

Step 3: combined with a boiler thermal performance test, the carbon emission of the direct carbon emission sources and the carbon emission of the indirect carbon emission sources are tested per hour in a test period.

According to different test purposes, the test can be generally divided into a boiler product carbon emission test, a boiler operation carbon emission test and a boiler acceptance carbon emission test.

The boiler greenhouse gas emission test and the boiler thermal performance test should be carried out simultaneously. For the boiler product carbon emission test, the average (converted) load of the boiler under each working condition should range from 97% to 105% of the rated load; the boiler operation carbon emission test should be carried out within the designed safe operation range of the boiler according to the actual operating load; the relevant test requirements of the boiler acceptance carbon emission test shall be determined by the acceptance parties through negotiation. For the boiler product carbon emission test, the maximum allowable fluctuation range of the boiler steam parameters is required according to the maximum allowable fluctuation range of the boiler rated steam parameters; for the boiler operation carbon emission test and the acceptance carbon emission test, the maximum allowable fluctuation range of the boiler steam parameters is required according to the maximum allowable fluctuation range of the operation steam parameters. The number of the boiler product carbon emission tests and the acceptance carbon emission tests is not less than 2, and the number of the boiler operation carbon emission tests is not less than 1. The test time is determined according to the combustion mode and the fuel type as follows: 1) for a room-fired boiler, the test time is not less than 4 h in the case of burning solid fuel, and the test time is not less than 2 h in the case of burning liquid or gas fuel; 2) for a layer-fired boiler, the test time is not less than 5 h (at least one complete slag deslagging cycle) in the case of hand firing or underfeeding, and the test time is not less than 4 h for other manners; 3) for a fluidized bed boiler, the test time is not less than 4 h; and 4) for an electric heating boiler, the test time is not less than 1 h.

(1) The specific process of testing the carbon emission of direct carbon emission sources per hour in the test period is as follows:

The amount of carbon dioxide directly emitted during the combustion and desulfurization and denitrification of the boiler fuel (excluding biomass) is determined by a measurement method and verified by an emission factor method, and the difference therebetween should not exceed 5%, which satisfies formula (1).

$$\frac{|E_{dm} - E_{dc}|}{E_{dm}} \leq 5\% \tag{1}$$

where:

$E_{dm}$—a direct emission measured value of carbon dioxide produced by the boiler, kg $CO_2$/h;

$E_{dc}$—a direct emission calculated value of carbon dioxide produced by the boiler, kg $CO_2$/h.

Measurement:

The measurement method measures the $CO_2$ content and the flue gas flow rate in the flue gas, to calculate the direct emission of carbon dioxide according to formula (2):

$$E_{dm} = \frac{1.9638 \cdot \varphi_{CO_2 \cdot fg.d} \cdot V'_{fg.d}}{100} \tag{2}$$

where:

1.9638—a carbon dioxide density in a standard state, kg/m$^3$;

$\varphi_{CO_2 fg.d}$—a volume fraction of $CO_2$ in the dry flue gas, %;

$$V'_{fg.d}$$

—a volume flow of the dry flue gas in the standard state, m$^3$/h, which can be determined by a direct measurement method or an indirect calculation method.

For coal and biomass mixed combustion boilers, the direct emission of carbon dioxide is calculated according to formula (3):

$$E_{dm.b} = \frac{1.9638 \cdot \varphi_{CO_2.fg.d} \cdot V'_{fg.d}}{100} \cdot \frac{\varphi_c\left(\omega_{C.ar.c} - \omega_{as.ar.c}\frac{\omega_{c.rs.m}}{100}\right)}{\varphi_b\left(\omega_{C.ar.b} - \omega_{as.ar.b}\frac{\omega_{c.rs.m}}{100}\right) + \varphi_c\left(\omega_{C.ar.c} - \omega_{as.ar.c}\frac{\omega_{c.rs.m}}{100}\right)} \tag{3}$$

where:

$E_{dm.b}$—a direct emission measured value of carbon dioxide produced by the coal and biomass mixed combustion boiler, kg $CO_2$/h;

$\varphi_b$, $\varphi_c$—mass proportions of biomass and coal in the mixed fuel respectively, %;

$\omega_{C.ar.b}$, $\omega_{C.ar.c}$—mass fractions of carbon in biomass and coal fuel (as received basis) respectively, %;

$\omega_{as.ac.b}$, $\omega_{as.sc.b}$—mass fractions of ash in biomass and coal fuels (as received basis) respectively, %;

$\omega_{c.rs.m}$—a mass fraction of average combustible content in ash, %, which is calculated by formula (4):

$$\omega_{c.rs.m} = \frac{\omega_s \omega_{c.s}}{100 - \omega_{c.s}} + \frac{\omega_{cl}\omega_{c.cl}}{100 - \omega_{c.cl}} + \frac{\omega_{as}\omega_{c.as}}{100 - \omega_{c.as}} \tag{4}$$

where:

$\omega_s$, $\omega_{el}$, $\omega_{as}$—mass fractions of slag, unburned coal and fly ash in the total ash content of fuel respectively, %;

$\omega_{c.s}$, $\omega_{c.cl}$, $\omega_{c.as}$—mass fractions of combustible content in slag, unburned coal and fly ash respectively, %.

In this embodiment, the direct measurement method of dry flue gas volume flow is to obtain the dry flue gas volume flow by measuring the flue gas volume flow and the $H_2O$ content in the flue gas, which is calculated according to formula (5):

$$V'_{fg.d} = \frac{V'_{fg}\left(100 - \varphi_{H_2O.fg}\right)}{100} \tag{5}$$

where:

$\varphi_{H_2O.fg}$—a volume fraction of $H_2O$ in the flue gas, %, $$V'_{fg}$$

—the flue gas volume flow, m$^3$/h.

In this embodiment, the indirect calculation method of dry flue gas volume flow is to calculate the dry flue gas volume flow generated by fuel combustion according to the boiler thermal performance test method, which is calculated according to formula (6):

$$V'_{fg.d} = B \cdot V_{fg.d} \tag{6}$$

where:

B—a fuel consumption per hour in the boiler test period, kg/h or m$^3$/h, which can be directly measured or calculated through the thermal performance test, preferably through the thermal performance test;

$V_{fg.d}$—a volume of the dry flue gas generated by the fuel combustion per kilogram or cubic meter, m$^3$/kg or m$^3$/m$^3$, which is calculated according to formula (7):

$$V_{fg.d} = V_{fg.d.th} + (\alpha - 1)V_{a.d.th} \tag{7}$$

where:

$V_{fg.d.th}$—a theoretical amount of the dry flue gas, m$^3$/kg or m$^3$/m$^3$;

$V_{a.d.th}$—a theoretical amount of dry air, m$^3$/kg or m$^3$/m$^3$;

$\alpha$—an excess air coefficient at the flue exhaust.

For solid and liquid fuels, the theoretical amount of the dry air and the theoretical amount of the dry flue gas are calculated from the actually burned carbon according to formulas (8) and (9) respectively. The theoretical amount of the dry air and the theoretical amount of the dry flue gas need to be corrected accordingly after adding desulfurizer:

$$V_{a.d.th} = 0.0888\omega_{c.b} + 0.0333\omega_{S.ar} + 0.2647\omega_{H.ar} - 0.0334\omega_{O.ar} \tag{8}$$

$$V_{fg.d.th} = 1.8658\frac{\omega_{c.b}}{100} + 0.6989\frac{\omega_{S.ar}}{100} + 0.79V_{a.d.th} + 0.8000\frac{\omega_{N.ar}}{100} \tag{9}$$

where:

$\omega_{c.b}$—a mass fraction of the actually burned carbon in the fuel fed into the furnace, %, which is calculated according to formula (10);

$\omega_{S.ar}$, $\omega_{H.ar}$, $\omega_{O.ar}$, $\omega_{N.ar}$—mass fractions of sulfur, hydrogen, oxygen and nitrogen in the fuel (as received basis) fed into the furnace, respectively, %;

$$\omega_{c.b} = \omega_{C.ar} - \frac{\omega_{as.ar}}{100}\omega_{c.rs.m} \tag{10}$$

where:

$\omega_{C.ar}$—a mass fraction of carbon in the fuel (as received basis) fed into the furnace, %;

$\omega_{as.at}$—a mass fraction of ash in fuel (as received basis) fed into the furnace, %.

For gas fuel, the theoretical amount of the dry air and the theoretical amount of the dry flue gas are calculated according to formulas (11) and (12):

$$V_{a.d.th} = \frac{1}{21}\left(0.5\varphi_{CO.g} + 0.5\varphi_{H_2.g} + 1.5\varphi_{H_2S.g} + \sum\left(m + \frac{n}{4}\right)\varphi_{C_mH_n.g} - \varphi_{O_2.g}\right) \tag{11}$$

$$V_{fg.d.th} = \frac{\varphi_{CO_2.g} + \varphi_{CO.g} + \varphi_{H_2S.g} + \sum m\varphi_{C_mH_n.g}}{100} + 0.79V_{a.d.th} + \frac{\varphi_{N_2.g}}{100} \tag{12}$$

where:

$\varphi_{CO.g}$, $\varphi_{H_2.g}$, $\varphi_{H_2S.g}$, $\varphi_{C_mH_n g}$, $\varphi_{O_2.g}$, $\varphi_{CO_2.g}$, $\varphi_{N_2.g}$—volume fractions of CO, $H_2$, $H_2S$, $C_mH_n$, $O_2$, $CO_2$ and $N_2$ in the gas fuel respectively, %.

Calculation:

The emission factor method is to calculate the direct carbon emission of carbon dioxide by measuring/calculating the consumption of fuels, desulfurizers and urea and the carbon emission factors in the process of fuel combustion, desulfurization and denitrification, which is calculated according to formula (13):

$$E_{dc} = B \cdot EF + B_{des} \cdot EF_{des} + B_{ur} \cdot EF_{ur} \quad (13)$$

where:

$B_{des}$—a desulfurizer consumption per hour in the boiler test period, kg/h;

$B_{ur}$—an urea consumption per hour in the boiler test period, kg/h;

$EF_{des}$—a carbonate emission factor in the desulfurizer, kg $CO_2$/kg;

$$EF_{des} = \frac{44}{10000} \frac{I_{CO3} \cdot \eta_{CO3.dec}}{M_{CO3}} \quad (14)$$

$I_{CO3}$—a content of carbonate in the desulfurizer, %;

$\eta_{CO3.dec}$—a decomposition rate of carbonate in the desulfurizer, %;

$M_{CO3}$—a molecular weight of the carbonate;

$EF_{ur}$—an urea emission factor, kg $CO_2$/kg;

$$EF_{ur} = \frac{44}{60} \cdot \frac{\eta_{ur.dec}}{100} \quad (15)$$

$\eta_{ur,dec}$—an urea decomposition rate, %.

EF—a carbon dioxide emission factor of the boiler fuel combustion, kg $CO_2$/kg or kg $CO_2/m^3$, which is calculated according to formula (16) or (17);

For the solid fuel and the liquid fuel:

$$EF = \frac{\omega_{C.ar}}{100} \cdot \frac{OF}{100} \cdot \frac{44}{12} \quad (16)$$

For the gas fuels:

$$EF = \rho_{CO_2.d} \cdot \frac{\varphi_{CO.g} + \varphi_{CO_2.g} + \sum m\varphi_{C_mH_n.g}}{100} \cdot \frac{OF}{100} \quad (17)$$

OF—a carbon oxidation rate of fuel, %.

In this embodiment, the fuel consumption B in the boiler test period of the emission factor method can be directly measured, or calculated by the thermal performance test, preferably calculated by the thermal performance test.

Preferably, the carbon oxidation rate of the solid fuel is calculated according to formula (18):

$$OF = 100 - \frac{\omega_{as.ar}}{\omega_{C.ar}}\left(\frac{\omega_s\omega_{c,s}}{100-\omega_{c.s}} + \frac{\omega_{cl}\omega_{c.cl}}{100-\omega_{c.cl}} + \frac{\omega_{as}\omega_{c.as}}{100-\omega_{c,as}}\right) \quad (18)$$

Preferably, the carbon oxidation rate of the liquid or gas fuel is calculated according to formula (19):

$$OF = \frac{100\varphi_{CO_2.fg.d}}{\varphi_{CO.fg.d} + \varphi_{CO_2.fg.d} + \sum m\varphi_{C_mH_n.fg.d}} \quad (19)$$

where:

$\varphi_{CO.fg.d}$, $\varphi_{C_mH_n fg.d}$—volume fractions of CO and $C_mH_n$ in the dry flue gas respectively, %.

(2) The specific process of testing the carbon emission of the indirect carbon emission sources per hour in the test period is as follows:

The indirect carbon emission refers to the carbon dioxide emission corresponding to the power used by the boiler, which is calculated according to formula (20):

$$E_{id} = \frac{AD_e \times EF_e}{T} \quad (20)$$

where:

$AD_e$—a total power consumption of the boiler system, kW·h;

$EF_e$—a carbon emission factor of power supply, kg $CO_2$/(kW·h).

T—a test condition duration, h.

In this embodiment, when the test boundary is the Boundary 1, a power consumption of the fan outside the system required to overcome the flue wind resistance in the boiler heat balance system is calculated according to formula (21):

$$AD_{ef} = \sum \frac{\Delta P_g}{\Delta P_f} \frac{\rho_f}{\rho_g} AD_f \quad (21)$$

where:

$AD_{ef}$—the power consumption of the fan outside the system required to overcome the flue wind resistance in the boiler heat balance system, kW·h;

$AD_f$—a power consumption of each fan, kW·h;

$\Delta P_g$—the flue wind resistance in the boiler heat balance system, kPa;

$\Delta P_f$—a fan pressure, kPa;

$\rho_f$—an average density of the air or flue gas at the inlet and outlet of the fan, $kg/m_3$;

$\rho_g$—an average density of the air or flue gas in the boiler heat balance system, $kg/m_3$;

A power consumption of a pump outside the system required to overcome the steam water resistance in the boiler heat balance system is calculated according to formula (22):

$$AD_{ep} = \sum \frac{\Delta P_w}{\Delta P_p} AD_p \quad (22)$$

where:

$AD_{ep}$—the power consumption of the pump outside the system required to overcome the steam water resistance in the boiler heat balance system, kW·h;

$AD_p$—a power consumption of each pump, kW·h;

$\Delta P_w$—the steam water resistance in the boiler heat balance system, kPa;

$\Delta P_p$—a pressure rise at the inlet and outlet of the pump, kPa.

The summary is as follows: testing the carbon emission of the direct carbon emission sources per hour in a test period specifically includes:

- combined with the boiler thermal performance test, carrying out a carbon emission test of the boiler system simultaneously or independently; wherein the carbon emission test is at least one of a boiler product carbon emission test, a boiler operation carbon emission test and a boiler acceptance carbon emission test;
- determining a carbon emission calculated value of the direct carbon emission sources every hour in the test period using an emission factor method;
- determining a volume flow of dry flue gas in the standard state using a direct measurement method or an indirect calculation method;
- determining a carbon emission measured value of the direct carbon emission sources per hour in the test period according to the volume flow of the dry flue gas in the standard state;
- if the carbon emission measured value and the carbon emission calculated value meet $$\frac{|E_{dm} - E_{dc}|}{E_{dm}} \leq 5\%,$$

determining the carbon emission measured value as the carbon emission of the direct carbon emission source every hour in the test period; where $E_{dm}$ is the carbon emission measured value, and $E_{dc}$ is the carbon emission calculated value;

- if the carbon emission measured value and the carbon emission calculated value meet $$\frac{|E_{dm} - E_{dc}|}{E_{dm}} > 5\%,$$

returning to the step of "determining the carbon emission calculated value of the direct carbon emission sources every hour in the test period using the emission factor method".

Step 4: a total carbon emission of the boiler per hour in the test period is calculated according to the carbon emission of the direct carbon emission sources and the carbon emission of the indirect carbon emission sources per hour in the test period.

The total carbon emission of the boiler per hour in the test period is calculated according to formula (23):

$$E = E_{dm} - E_{id} \tag{23}$$

Step 5: a carbon emission intensity of the boiler per unit output heat is determined according to the total carbon emission of the boiler per hour in the test period.

The carbon emission intensity of the boiler per unit heat output is calculated according to formula (24):

$$E_a = \frac{1}{3.6} \cdot \frac{E}{Q} \tag{24}$$

where:

$E_a$—the carbon dioxide emission intensity per unit output heat, kg $CO_2$/GJ;

Q—an output thermal power of the boiler, MW.

Taking a 20 t/h coal-fired steam boiler as an example, the method for calculating carbon emission of the boiler is further illustrated.

In step 1, the combustion mode is a layer combustion, and the Boundary 1 is selected as the test boundary.

In step 2, the direct carbon emission is the carbon dioxide emission generated in the process of fuel (excluding biomass) combustion and desulfurization and denitrification, and the indirect carbon emission is the carbon dioxide emission corresponding to the power consumption of the boiler.

The emission source only considers the direct carbon emission generated by the fuel combustion in the boiler proper.

In step 3, the boiler carbon emission test and the boiler thermal performance test are carried out simultaneously. The key parameters needed in the boiler carbon emission test and calculation can be obtained during the thermal performance test. On the one hand, carrying out the boiler carbon emission test and the boiler thermal performance test simultaneously is conducive to the accurate quantification of carbon emission, and on the other hand, is conducive to the coordination of the carbon emission test and the thermal efficiency test.

In the preferred embodiment of the present disclosure, the boiler carbon emission test and the boiler thermal performance test are carried out simultaneously. The direct carbon emission of the boiler is determined by the measurement method and verified by the emission factor method. The volume flow of dry flue gas required by the measurement method is determined by the indirect calculation method. The calculated volume $V_{fg.d}$ of dry flue gas generated by fuel combustion per kilogram at the flue outlet is 8.08 $m^3$/kg, the fuel consumption B in the test period is 2826 kg/h, the volume flow $$V'_{fg.d}$$

of dry flue gas in the standard state is 22834 $m^3$/h, the $CO_2$ content $\varphi_{CO_2,fg.d}$ in dry flue gas is 11.3%, and the direct emission measured value $E_{dm}$ of carbon dioxide generated by the boiler is 5067 kg $CO_2$/h. The emission factor method only considers the carbon dioxide produced by the fuel combustion, the carbon oxidation rate OF of the fuel is 0.9237, the carbon dioxide emission factor of the fuel is 1.799 kg $CO_2$/kg, and the direct emission calculated value of carbon dioxide produced by the boiler is 5084 kg $CO_2$/h. The difference between the measurement method and the emission factor method is 0.34%, which meets the requirement of no more than 5%.

In step 4, for the selected test boundary and carbon emission sources, the direct and indirect carbon emissions of each emission source in the test period are summed to obtain the total carbon emission of the boiler per hour in the test period.

In the preferred embodiment of the present disclosure, only the direct carbon emission is considered, and the total carbon emission of the boiler per hour in the test period is 5067 kg $CO_2$/h.

In step 5, the carbon emission intensity of the boiler per unit output heat is calculated through the total carbon emission of the boiler per hour and the output heat of the boiler per hour in the test period.

The output heat of the boiler per hour is 48.2 GJ/h, the total carbon emission of the boiler per hour in the test period is 5067 kg $CO_2$/h, and the carbon emission intensity of the boiler per unit output heat is 105.1 kg $CO_2$/GJ.

Compared with the prior art, the present disclosure has the following beneficial effects:

1. The present disclosure provides a method for testing and calculating the carbon emission of the boiler, which can solve the problem that there is no accurate quantification method of the carbon emission of the boiler in the prior art.
2. The proposed method for testing and calculating the carbon emission fully combines the existing performance test methods, and obtains the carbon emission characteristics of the boiler while testing the thermal efficiency.
3. The proposed method for testing and calculating the carbon emission fully considers different test boundaries and emission sources, and can meet the quantitative requirements of carbon emission of different boiler systems.
4. When the method for testing and calculating the carbon emission proposed by the present disclosure is used, the carbon emission intensity of different boiler products and operating conditions can be compared and analyzed, which provides a reference for formulating energy-saving and carbon-reducing measures.

Various embodiments in this specification are described in a progressive way. Each embodiment focuses on the differences from other embodiments, and the same and similar parts of various embodiments can be referred to each other.

In the present disclosure, specific examples are used to illustrate the principle and implementation of the present disclosure, and the description of the above embodiments is only used to help understand the method and core ideas of the present disclosure. Meanwhile, according to the idea of the present disclosure, there will be some changes in the specific implementation and application scope for those skilled in the art. To sum up, the contents of the specification should not be construed as limiting the present disclosure.

What is claimed is:

1. A method for calculating carbon emission of a boiler, comprising:

determining a test boundary of a boiler system and carbon emission sources in the test boundary; wherein the test boundary is a boiler heat balance system boundary or a boiler system boundary; the boiler heat balance system boundary comprises a boiler proper, a steam water system circulating pump, a direct-fired pulverizing system coal mill, a denitration device, a flue gas recirculation fan and a slag cooler; the boiler proper is an integrity comprising a boiler barrel, a vapor liquid separator and a water storage tank, a heating surface, a header, a connecting pipeline, a furnace, a combustion device, an air preheater, a furnace wall, a flue and a framework; and the boiler system boundary comprises the boiler proper and a plurality of auxiliary devices, wherein a working medium side boundary uses a heat balance boundary; the plurality of auxiliary devices comprise fans, pumps, fuel preparation devices, fuel supply devices, ash and slag removal devices, flue gas purification devices and control devices;

dividing the carbon emission sources in the test boundary into direct carbon emission sources and indirect carbon emission sources; wherein when the test boundary is the boiler heat balance system boundary, the carbon emission of the direct carbon emission sources comprises direct carbon emission generated by combusting and performing desulfurization and denitrification on fuel without biomass in the boiler heat balance system boundary; the carbon emission of the indirect carbon emission sources comprises indirect carbon emission generated by power consumption of an electric heating device and an auxiliary device in the boiler heat balance system and corresponding indirect carbon emission generated by power consumption of an auxiliary device outside a system required to overcome a flue wind resistance and a steam water resistance in the boiler heat balance system; and when the test boundary is the boiler system boundary, the carbon emission of the direct carbon emission source comprises direct carbon emission generated by combusting and performing desulfurization and denitrification on the fuel without biomass in the boiler system boundary; the carbon emission of the indirect carbon emission sources comprise indirect carbon emission generated by power consumption of all related electric heating devices and auxiliary devices;

combined with a boiler thermal performance test, testing a carbon emission of the direct carbon emission sources and a carbon emission of the indirect carbon emission sources per hour in a test period;

wherein testing the carbon emission of the direct carbon emission sources per hour in the test period comprises:

combined with the boiler thermal performance test, carrying out a carbon emission test of the boiler system simultaneously or independently; wherein the carbon emission test is at least one of a boiler product carbon emission test, a boiler operation carbon emission test and a boiler acceptance carbon emission test;

determining a carbon emission calculated value of the direct carbon emission sources every hour in the test period using an emission factor method according to:

$$E_{dc} = B \cdot EF + B_{des} \cdot EF_{des} + B_{ur} \cdot EF_{ur}$$

wherein B is a fuel consumption per hour in a boiler test period, EF is a carbon dioxide emission factor of boiler fuel combustion, $B_{des}$ is a desulfurizer consumption per hour in the boiler test period, $EF_{des}$ is a carbonate emission factor in the desulfurizer, $B_{ur}$ is an urea consumption per hour in the boiler test period, and $EF_{ur}$ is an urea emission factor;

determining a volume flow of dry flue gas in a standard state using a direct measurement method or an indirect calculation method;

determining a carbon emission measured value of the direct carbon emission sources per hour in the test period according to the volume flow of the dry flue gas in the standard state, comprising:

if the fuel does not comprise biomass, a calculation formula of determining a direct carbon emission measured value generated by fuel combustion and desulfurization and denitrification in the boiler heat balance system boundary according to the volume flow of the dry flue gas in the standard state is as follows:

$$E_{dm,a}=\frac{1.9638\cdot\varphi_{CO_2.fg.d}\cdot V'_{fg.d}}{100}$$

wherein $E_{dm,a}$ is the direct carbon emission measured value generated by combusting and performing desulfurization and denitrification on the fuel without biomass in the boiler heat balance system boundary, $\varphi_{co_2.fg.d}$ is a volume fraction of carbon dioxide in the dry flue gas, and $V_{fg.d}'$ is a volume flow of the dry flue gas in the standard state;

if the fuel is mixed with biomass, a calculation formula of determining the direct carbon emission measured value generated by combusting and performing desulfurization and denitrification on the fuel without biomass in the boiler heat balance system boundary according to the volume flow of the dry flue gas in the standard state is as follows:

$$E_{dm.b}=\frac{1.9638\cdot\varphi_{co_2.fg.d}\cdot V'_{fg.d}}{100}\cdot\frac{\varphi_c\left(\omega_{C.ar.c}-\omega_{as.ar.c}\frac{\omega_{c.rs.m}}{100}\right)}{\varphi_b\left(\omega_{C.ar.b}-\omega_{as.ar.b}\frac{\omega_{c.rs.m}}{100}\right)+\varphi_c\left(\omega_{C.ar.c}-\omega_{as.ar.c}\frac{\omega_{c.rs.m}}{100}\right)}$$

wherein $E_{dm.b}$ is the direct carbon emission measured value generated by combusting and performing desulfurization and denitrification on the fuel without biomass in the boiler heat balance system boundary when the fuel is mixed with biomass, $\varphi_b$ and $\varphi_c$ are mass proportions of biomass and coal in a mixed fuel, respectively, $\omega_{C.ar.b}$ and $\omega_{C.ar.c}$ are mass fractions of carbon in biomass and coal fuels, respectively, $\omega_{as.ar.b}$ and $\omega_{as.ar.c}$ are mass fractions of ash in the biomass and coal fuels, respectively, and $\omega_{c.rs.m}$ is a mass fraction of average combustible content in ash;

if the carbon emission measured value and the carbon emission calculated value meet $$\frac{|E_{dm}-E_{dc}|}{E_{dm}}\leq 5\%,$$

determining the carbon emission calculated value meet measured value as the carbon emission of the direct carbon emission source every hour in the test period; where $E_{dm}$ is the carbon emission measured value, and $E_{dc}$ is the carbon emission calculated value; and if the carbon emission measured value and the carbon emission calculated value meet $$\frac{|E_{dm}-E_{dc}|}{E_{dm}}>5\%,$$

returning to the step of determining the carbon emission calculated value of the direct carbon emission sources every hour in the test period using the emission factor method;

wherein testing the carbon emission of the indirect carbon emission sources per hour in the test period according to:

$$E_{id}=\frac{AD_e\times EF_e}{T}$$

wherein $E_{id}$ is the carbon emission of the indirect carbon emission sources, $AD_e$ is a total power consumption of the boiler system, $EF_e$ is a carbon emission factor of power supply, and T is a test condition duration;

wherein when the test boundary is the boiler heat balance system boundary, $$AD_e=AD_{ef}+AD_{ep}+AD_{el};$$

wherein $AD_{el}$ is the indirect carbon emission corresponding to the power consumption of the auxiliary device within the boiler heat balance system boundary;

a calculation formula of the indirect carbon emission $AD_{ef}$ corresponding to power consumption of the auxiliary device outside system required to overcome a flue wind resistance in the boiler heat balance system is as follows:

$$AD_{ef}=\sum\frac{\Delta P_g}{\Delta P_f}\frac{\rho_f}{\rho_g}AD_f$$

wherein $\Delta P_g$ is the flue wind resistance in the boiler heat balance system, $\Delta P_f$ is a fan pressure, $\rho_f$ is an average density of air or flue gas at an inlet and outlet of the fan, $\rho_g$ is an average density of the air or flue gas in the boiler heat balance system, and $AD_f$ is a power consumption of each fan;

a calculation formula of the indirect carbon emission $AD_{ep}$ corresponding to power consumption of the auxiliary device outside the system required to overcome a steam water resistance in the boiler heat balance system is as follows:

$$AD_{ep}=\sum\frac{\Delta P_w}{\Delta P_p}AD_p$$

wherein $\Delta P_w$ is the steam water resistance in the boiler heat balance system, $\Delta P_p$ is a pressure rise at an inlet and outlet of a pump, and $AD_{ep}$ is the power consumption of the pump outside the system required to overcome the steam water resistance in the boiler heat balance system;

calculating a total carbon emission of the boiler per hour in the test period according to the carbon emission of the direct carbon emission sources and the carbon emission of the indirect carbon emission sources per hour in the test period; and wdetermining a carbon emission intensity of the boiler per unit output heat according to the total carbon emission of the boiler per hour in the test period.

2. The method for calculating carbon emission of the boiler according to claim 1, wherein a calculation formula of the total carbon emission of the boiler per hour in the test period is as follows:

$$E = E_{dm} + E_{id}$$

where E is the total carbon emission of the boiler per hour in the test period.

3. The method for calculating carbon emission of the boiler according to claim 2, wherein a calculation formula of the carbon emission intensity of the boiler per unit output heat is:

$$E_a = \frac{1}{3.6} \cdot \frac{E}{Q}$$

where $E_a$ is the carbon emission intensity of the boiler per unit output heat, and Q is an output thermal power of the boiler.

* * * * *